US005736372A

United States Patent [19]
Vacanti et al.

[11] Patent Number: 5,736,372
[45] Date of Patent: Apr. 7, 1998

[54] BIODEGRADABLE SYNTHETIC POLYMERIC FIBROUS MATRIX CONTAINING CHONDROCYTE FOR IN VIVO PRODUCTION OF A CARTILAGINOUS STRUCTURE

[75] Inventors: Joseph P. Vacanti, Winchester; Charles A. Vacanti, Lexington; Robert S. Langer, Newton, all of Mass.

[73] Assignees: Massachusetts Institute of Technology, Cambridge; Children's Medical Center Corporation, Boston, both of Mass.

[21] Appl. No.: 509,952

[22] Filed: Apr. 16, 1990

Related U.S. Application Data

[63] Continuation-in-part of Ser. No. 339,155, Apr. 17, 1989, Pat. No. 5,041,138, which is a continuation-in-part of Ser. No. 123,579, Nov. 20, 1987, abandoned, which is a continuation-in-part of Ser. No. 933,018, Nov. 20, 1986, abandoned.

[51] Int. Cl.$^6$ .................. C12N 11/08; C12N 5/00; A61F 2/28; A61F 2/18
[52] U.S. Cl. .................. 435/180; 424/93.7; 424/422; 424/426; 424/548; 424/549; 435/177; 435/178; 435/395; 435/398; 435/402
[58] Field of Search .................. 435/174, 177, 435/178, 180, 182, 395, 398, 402; 623/10, 16, 18; 424/93.7, 548, 549, 422, 426; 514/21; 530/840

[56] References Cited

U.S. PATENT DOCUMENTS

| | | | |
|---|---|---|---|
| 4,144,126 | 3/1979 | Burbidge | 195/1.1 |
| 4,228,243 | 10/1980 | Iizuka | 435/285 |
| 4,356,261 | 10/1982 | Kuettner | 435/68 |
| 4,485,097 | 11/1984 | Bell | 424/95 |
| 4,505,266 | 3/1985 | Yannas et al. | 128/1 R |
| 4,520,821 | 6/1985 | Schmidt et al. | 128/334 R |
| 4,553,272 | 11/1985 | Mears | 623/1 |
| 4,609,551 | 9/1986 | Caplan et al. | 424/95 |
| 4,642,120 | 2/1987 | Nevo et al. | 623/16 |
| 4,713,070 | 12/1987 | Mano | 623/1 |
| 4,757,017 | 7/1988 | Cheung | 435/240.23 |
| 4,778,749 | 10/1988 | Vasington et al. | 435/2 |
| 4,846,835 | 7/1989 | Grande | 623/11 |

FOREIGN PATENT DOCUMENTS

| | | |
|---|---|---|
| 0226061 | 11/1986 | European Pat. Off. |
| 62-011459 | 1/1987 | Japan |
| 63-196273 | 8/1988 | Japan |
| 63-196595 | 8/1988 | Japan |
| WO 87/06120 | 4/1987 | WIPO |
| WO 89/00413 | 7/1988 | WIPO |

OTHER PUBLICATIONS

Vacanti et al J. Ped. Surgery 23(1) 3–9 1988.
Leeson et al *Histology* 3rd et W.B. Saunders Co pp. 86, 87, 114 1976.
Thuroff et al Urology 21(2): 155–157 1983.
J.M. Wozney, et al., *Science* 242, 1528–1534 (Dec. 16, 1988).
J. Upton, *Plastic and Reconstructive Surgery* 68(2), 166–174 (1981).
Alberts, et al., *Molecular Biology of the Cell*, 893 and 894 (1983).
Ptasinska–Urbanska, et al., *Exp. Eye Res.*, vol. 24, No. 3 pp. 241–247 (1977).

*Primary Examiner*—David M. Naff
*Attorney, Agent, or Firm*—Arnall Golden & Gregory, LLP

[57] ABSTRACT

Methods and artificial matrices for the growth and implantation of cartilaginous structures and surfaces and bone are disclosed. In the preferred embodiments, chondrocytes are grown on biodegradable, biocompatible fibrous polymeric matrices. Optionally, the cells are proliferated in vitro until an adequate cell volume and density has developed for the cells to survive and proliferate in vivo. One advantage of the matrices is that they can be cast or molded into a desired shape, on an individual basis, so that the final product closely resembles a patient's own ear or nose. Alternatively, flexible matrices can be used which can be manipulated at the time of implantation, as in a joint, followed by remodeling through cell growth and proliferation in vivo. The cultured cells can also be maintained on the matrix in a nutrient media for production of bioactive molecules such as angiogenesis inhibiting factor. Examples are provided showing the growth of hyaline cartilage for joint relinings, the growth of elastic cartilage for plastic or reconstructive replacement of cartilage structures, and repair of large bone defects.

15 Claims, 9 Drawing Sheets

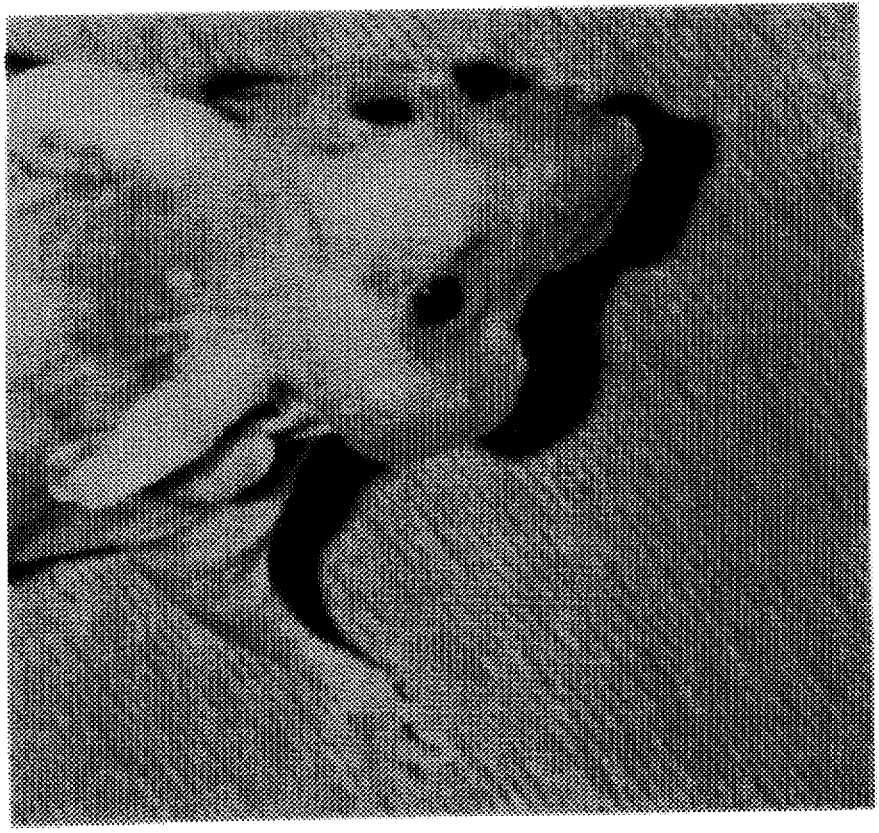
FIG.IA
AFTER
FIG.IA
BEFORE

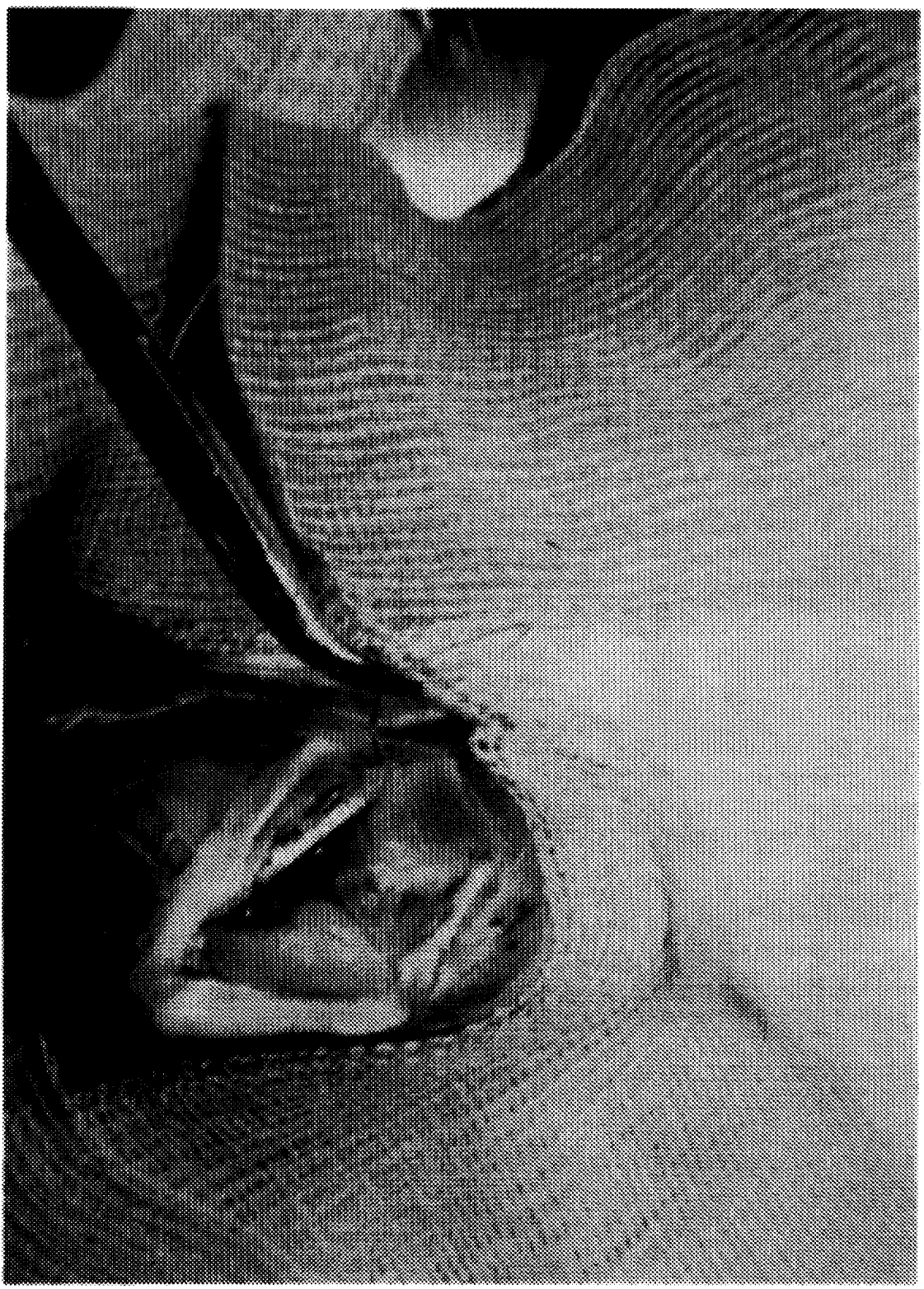
FIG.IOA

BIODEGRADABLE SYNTHETIC POLYMERIC FIBROUS MATRIX CONTAINING CHONDROCYTE FOR IN VIVO PRODUCTION OF A CARTILAGINOUS STRUCTURE

This application is a continuation-in-part of application Ser. No. 07/339,155, filed Apr. 17, 1989, now U.S. Pat. No. 5,041,138, which is a continuation-in-part of application Ser. No. 07/123,579, filed Nov. 20, 1987, now abandoned, which is a continuation-in-part of application Ser. No. 06/933,018, filed Nov. 20, 1986, now abandoned.

The United States Government has rights in this invention by virtue of NIH grant No. 6M 26698.

BACKGROUND OF THE INVENTION

This is generally in the field of medicine and cell culture, and in particular in the area of implantable cartilaginous structures formed on biocompatible artificial matrices.

U.S. Ser. No. 07/123,579 entitled Chimeric Neomorphogenesis of Organs by Controlled Cellular Implantation Using Artificial Matrices filed Nov. 20, 1987, and U.S. Ser. No. 06/933,018 entitled "Chimeric Neomorphogenesis of Organs Using Artificial Matrices" filed Nov. 20, 1986, by Joseph P. Vacanti and Robert S. Langer describe a method and means whereby cells having a desired function are grown on polymer scaffolding shaped to maximize surface area to allow adequate diffusion of nutrients and growth factors to the cells, so that the maximum distance over which adequate diffusion through densely packed cells can occur is in the range of approximately 100 to 300 microns, using cell culture techniques, followed by transfer of the cell-polymer scaffold into a patient at a site appropriate for attachment, growth and function, after attachment and equilibration, to produce a functional organ equivalent. Success depends on the ability of the implanted cells to attach to the surrounding environment and to stimulate angiogenesis. Nutrients and growth factors are supplied during cell culture allowing for attachment, survival or growth as needed.

After the structure is implanted and growth and vascularization take place, the resulting organoid is a chimera formed of parenchymal elements of the donated tissue and vascular and matrix elements of the host. The polymer scaffolding used for the initial cell culture is constructed of a material which degrades over time and is therefore not present in the chimeric organ. Vascular ingrowth following implantation allows for normal feedback mechanisms controlling the soluble products of the implanted cells. The preferred material for forming the matrix or support structure is a biodegradable artificial polymer, for example, polyglycolic acid, polyorthoester, or polyanhydride, which is degraded by hydrolysis at a controlled rate and reabsorbed. These materials provide the maximum control of degradability, manageability, size and configuration, although other materials, including non-biodegradble materials such as teflon can be used. In some embodiments these materials are overlaid with a second material such as gelatin or agarose to enhance cell attachment. The polymer matrix must be configured to provide both adequate sites for attachment and adequate diffusion of nutrients from the cell culture to maintain cell viability and growth until the matrix is implanted and vascularization has occurred. The preferred structure for organ construction is a fibrous three dimensional structure formed of polymer fibers having a high surface area, which results in a relatively shallow concentration gradient of nutrients, wastes, and gases, so as to produce uniform cell growth and proliferation.

U.S. Ser. No. 06/933,018 and U.S. Ser. No. 07/123,579 disclose several examples of the successful culturing and implantation of hepatocytes and cells isolated from intestine and pancreas, with subsequent normal function, including production and secretion of bioactive molecules. Examples of such molecules include growth hormone from pituitary cells, insulin and glycogen from pancreatic cells, and clotting factors from liver cells. As described in these applications, however, there is a need for a different type of functioning "organ", one which provides primarily a structural function. Examples of types of cells which are useful in these applications include cartilage and bone precurser cells.

Damage of cartilage produced by disease, such as arthritis, or trauma is a major cause of physical deformity and debilitation. In medicine today, the primary therapy for loss of cartilage is replacement with a prosthetic material, such as silicone for cosmetic repairs, or metal alloys for joint relinement. Placement of prostheses is commonly associated with significant loss of underlying tissue and bone without recovery of the full function allowed by the original cartilage, as well as the irritating presence of a foreign body. Other long term problems associated with a permanent foreign body can include infection, erosion and instability.

The lack of truly biocompatible, functional prosthesis can have profound and tragic effects for those individuals who have lost noses or ears due to burns or trauma, such as car accidents or war. The best surgeons can do for these patients is to carve a piece of cartilage out of a piece of lower rib to approximate the necessary contours and insert it into a pocket of skin in the area where the nose or ear is missing.

In the past, bone has been replaced using actual segments of sterilized bone or bone powder or porous surgical steel seeded with bone cells which were then implanted. An example of a process using bone powder and a hydrated collagen lattice is U.S. Pat. No. 4,485,097 to Bell. An example of the implantation of a seeded porous metal prosthesis is U.S. Pat. No. 4,553,272 to Mears. The success of these implants has been limited, in part because of the non-degradable nature of the cell supports. Very little has ever been actually used to replace the cartilage overlaying bone surfaces. At this time, when cartilage is worn or damaged in a joint, there is no way to replace the cartilage, although International patent application WO 89/00413 published 26 Jan. 1989 does describe the use of a glycosaminogycan prosthetic meniscus for implantation in the knee that allows ingrowth of adjoining tissues. Despite several preparations being tested to stimulate growth and repair of the remaining cells, in most cases repair to injuries is made surgically. Patients suffering from degeneration of cartilage can only turn to drugs having analgesic or antiinflammatory properties, or compounds such as hyaluronic acid, for relief.

To date, the growth of new cartilage from either transplantation of autologous or allogeneic cartilage has been largely unsuccessful. Microscopic islands of cartilage formation have recently been demonstrated histologically in vivo by implanting recombinant bone morphogenic protein, as reported by J. M. Wozney, et al., *Science*, 242, 1528–1534, (Dec. 16, 1988). Limited success has been achieved in making neocartilage using free autogenous grafts of perichondrial flaps, as described by J. Upton, *Plastic and Reconstructive Surgery*, 68(2), 166–174, (August 1981). However, there have been no reports of successful growth of cartilage in vivo from cell culture.

It is therefore an object of the present invention to provide a method and means for designing, constructing and utilizing artificial matrices as temporary scaffolding for cellular growth and implantation of cartilage.

It is a further object of the invention to provide biodegradable, non-toxic matrices which can be utilized for cell growth, both in vitro and in vivo, as supports for cartilaginous structures.

It is a still further object of the invention to provide biodegradable, non-toxic matrices which can be utilized for cell growth, both in vitro and in vivo, to replace degenerated hyaline cartilage in joints and other places of surface-to-surface contact, and elastic cartilage for plastic and reconstructive surgery.

It is another object of this invention to provide an in vitro system in which cells will retain their normal morphology and cell function for the secretion of bioactive molecules normally produced in the body by those cells.

It is still another object of this invention to provide a method and means for growing new bone form cartilage cells implanted on biodegradable, non-toxic matrices

SUMMARY OF THE INVENTION

Methods and artificial matrices for the growth and implantation of cartilaginous structures and surfaces and the production of bioactive molecules manufactured by chondrocytes are disclosed. Also disclosed is a method and matrices for growing new bone from chondrocytes implanted on biodegradable matrices.

In the preferred embodiments, chondrocytes are grown in culture on fibrous matrices formed of biodegradable polymers, non-degradable materials, or a combination of the two. The cells can be cultured in vitro until an adequate cell volume and density has developed for the cells to survive and proliferate in vivo, or maintained in vitro for the purpose of manufacturing bioactive molecules, such as angiogenesis inhibiting factor. Alternatively, when adequate cell numbers for implantation are available, the cells can be attached to the matrix and implanted directly, without proliferation in vitro. One advantage of polymeric matrices is that they can be cast or molded into a desired shape on an individual basis, so that the final product closely resembles the patient's own ear or nose. Alternatively, flexible biodegradable matrices can be used which allow for manipulation at the time of implantation, as in a joint, followed by remodeling through cell growth and proliferation in vivo.

Examples are provided showing the growth of hyaline cartilage for joint relinings, the growth of elastic cartilage for plastic or reconstructive replacement of cartilage structures, and repair of large bone defects.

BRIEF DESCRIPTION OF THE DRAWINGS

FIGS. 1a and 1b are photographs of the head of a nude mouse implanted with a biodegradable matrix seeded with chondrocytes (FIG. 1a); and after five to six weeks of growth, showing cartilage plates underlying the skin (FIG 1b), demonstrating construction of facial contour plates.

FIG. 4a is a 4× magnification. FIG. 4b is a 20× magnification.

FIG. 9a is at 20×. FIG. 9b is at 4×.

FIGS. 10a and 10b are photographs showing construction of a knee joint lining in a rabbit: FIG. 10a, suturing in a polyglycolic acid surgical mesh seeded with chondrocytes overlaid with surgical mesh not seeded with chondrocytes; and FIG. 10b, showing formation of a cartilage plate after five weeks.

DETAILED DESCRIPTION OF THE INVENTION

Figure 1B:

As described in more detail below, dispersed chondrocytes, fibroblasts, and/or bone precursor cells are isolated and then mixed with a biocompatible matrix in vitro, for subsequent implantation in vivo to form a cartilaginous structure. In one embodiment, cells are incubated with the matrix until they attach to the surface and the matrix is then implanted at a surgically prepared recipient site. Methods for preparing the site are known to those skilled in the art of reconstructive and plastic surgery. In another embodiment, the cells are mixed with the matrix, incubated until the cells attach and proliferate to a desired volume, and then implanted.

The matrices are formed of a biodegradable, non-degradable, or combination of biodegradable and non-degradable materials which have been configured to produce high cell densities by allowing adequate diffusion of nutrients and waste as well as gas exchange, while in vitro or in vivo, prior to remodeling and integration with host tissue. Cartilage precurser cells, including chondrocytes, bone precursor cells, fibroblasts, and others, differ significantly from some types of cells, such as hepatocytes, in their requirements for nutrient and gas exchange. As a result, the matrices can be configured as tighter structures than structures utilized to implant hepatocytes.

Cartilage is a specialized type of dense connective tissue consisting of cells embedded in a matrix. There are several kinds of cartilage. Translucent cartilage having a homogeneous matrix containing collagenous fibers is found in articular cartilage, in costal cartilages, in the septum of the nose, in larynx and trachea. Articular cartilage is hyaline cartilage covering the articular surfaces of bones. Costal cartilage connects the true ribs and the sternum. Fibrous cartilage contains collagen fibers. Yellow cartilage is a network of elastic fibers holding cartilage cells which is primarily found in the epiglottis, the external ear, and the auditory tube. As described below, cartilage implants can be formed of one or more types of cartilage, depending primarily on the location of the implant and the type of cartilage cells seeded onto the matrix.

In the preferred method, polymer fibers are placed in culture media containing chondrocytes, where the chondrocytes attach to the fibers in multiple layers and retain their normal rounded configuration, which appears to be essential for the chondrocytes to maintain their normal function and secrete a cartilage matrix and other bioactive molecules such as angiogenesis inhibiting factor. This technique also allows transplantation of the polymer cell scaffold into animals without disrupting the complex of attached chondrocytes. Transplantation of this complex containing a high density of normally functioning chondrocytes with a large surface area into an animal allows the cells to obtain adequate nutrition by diffusion and successful engraftment of functioning chondrocytes with cartilage formation prior to remodeling and integration with the host tissue.

The examples below demonstrate that it is possible to grow in culture on fibers of biodegradable polymers chondrocytes that appear to be morphologically and functionally normal, and will proliferate to a cell density sufficient to allow implantation of the cell polymer scaffold in animals and successful engraftment with formation of a new tissue equivalent as the polymer resorbs.

In one example, visual and histologic characterization of this tissue show that it is hyaline cartilage (based on the presence of type II collagen rather than type I collagen), very similar to normal human fetal cartilage. In another example, chondrocytes obtained from biopsy of elastic cartilage attached to polymer structures and grew in the approximate dimensions of the implanted complex. In still another example, a bone defect was repaired by implantation in the defect of chondrocytes attached to a polymer structure, which grew into bone. The examples also demonstrate that the polymer fiber scaffold is essential in that neither injection of free chondrocytes nor implantation of the polymer fibers without attached chondrocytes results in cartilage formation. Associated with the development of this cartilage formation is a decrease in neovascularization and fibrous tissue formation, probably reflecting the production of an angiogenesis inhibiting factor by the newly formed cartilage, as has been demonstrated by assays of serum in which chondrocytes have been grown in vitro on fibers.

Chondrocytes are initially isolated and cultured using techniques known to those skilled in the art of tissue culture. In contrast to some types of cells, chondrocytes can be seeded directly onto an appropriate matrix and implanted without first proliferating the cells in vitro. If insufficient cell numbers are available for implantation, cells are first cultured in vitro on the matrix. Once the cells have begun to grow and cover the matrix, they are implanted in a patient at a site appropriate for attachment, growth and function. One of the advantages of a biodegradable polymeric matrix is that angiogenic and other bioactive compounds can be incorporated directly into the matrix so that they are slowly released as the matrix degrades in vivo. As the cell-polymer structure is vascularized and the structure degrades, the cells will differentiate according to their inherent characteristics.

In the preferred embodiment, the matrix is formed of a bioabsorbable, or biodegradable, synthetic polymer such as a polyanhydride, polyorthoester, polyglycolic acid, copolymers, blends, and combinations thereof. Collagen and crosslinked glycosaminoglycans can also be used as the support material. In some cases, non-biodegradable materials such as teflon, nylon, polyester, or ethylene vinyl acetate can also be used, alone, or in combination with biodegradable materials. Although not preferred in the replacement of linings of joints having surface-to-surface contact, the non-degradable materials have structural advantages in some cases, as in the formation of ears and noses.

Attachment of the cells to the polymer can be enhanced by coating the polymers with compounds such as basement membrane components, agar, agarose, gelatin, gum arabic, collagens, fibronectin, laminin, glycosaminoglycans, attachment peptides, mixtures thereof, and other materials having properties similar to biological matrix molecules known to those skilled in the art of cell culture. All polymers must meet the mechanical and biochemical parameters necessary to provide adequate support for the cells with subsequent growth and proliferation. Factors, including nutrients, growth factors, inducers of differentiation or de-differentiation, products of secretion, immunomodulators, inhibitors of inflammation, regression factors, biologically active compounds which enhance or allow ingrowth of the lymphatic network or nerve fibers, hyaluronic acid, and drugs, can be incorporated into the matrix or provided in conjunction with the matrix. Similarly, polymers containing peptides such as the attachment peptide RGD (Arg-Gly-Asp) can be synthesized for use in forming matrices.

A presently preferred polymer is polyglactin 910, developed as absorbable synthetic suture material, a 90:10 copolymer of glycolide and lactide, manufactured as Vicryl® braided absorbable suture (Ethicon, Inc., Somerville, N.J.) (Craig P. H., Williams J. A., Davis K. W., et al.: A Biological Comparison of Polyglactin 910 and Polyglycolic Acid Synthetic Absorbable Sutures. *Surg.* 141; 1010, (1975) ). A commercially available surgical mesh formed of polyglycolic acid, Dexon™, is preferred for use in construction of new joint linings.

The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy; with respect to toxicology by initial screening tests involving Ames assays and teratogenicity assays, and implantation studies in animals for immunogenicity, inflammation, release and degradation studies. In vitro cell attachment and viability can be assessed using scanning electron microscopy, histology, and quantitative assessment with radioisotopes.

Fibers (sutures or non-woven meshes) can be used as supplied by the manufacturer. Other shapes can be fabricated using one of the following methods:

Solvent Casting. A solution of polymer in an appropriate solvent, such as methylene chloride, is cast on a fibrous pattern relief structure. After solvent evaporation, a thin film is obtained.

Compression Molding. Polymer is pressed (30,000 psi) into an appropriate pattern.

Filament Drawing. Filaments are drawn from the molten polymer.

Meshing. A mesh is formed by compressing fibers into a felt-like material.

At the present time, a mesh-like structure formed of fibers which may be round, scalloped, flattened, star shaped, solitary or entwined with other fibers is preferred. The use of fibers is based upon the same principles which nature has used to solve the problem of increasing surface area proportionate to volume increases. All multicellular organisms utilize a repeating branching structure. Branching systems represent communication networks between organs as well as the functional units of individual organs. Seeding and implanting this type of configuration with cells allows implantation of large numbers of cells, each of which is exposed to the environment of the host, providing for free exchange of nutrients and waste while neovascularization is achieved. An average interfiber distance between approximately 100 and 300 microns is preferred since the maximum distance over which adequate diffusion of nutrients and growth factors can occur to cells through densely packed cells is in a range of approximately 100 to 300 microns.

The polymeric matrix may be made flexible or rigid, depending on the desired final form, structure and function. For purposes of making a nose or ear, fibers or sheets of felt-like or solid material are cut to approximate the plates of cartilage. Either woven, non-woven or knitted material can be used. A material such as a velour is an example of a suitable woven material. The fibers can be fused together by addition of a solvent or melting to form a more stable structure. Alternatively, high pressure jets of water onto a fibrous mat can be used to entangle the fibers to form a more rigid structure. For resurfacing a joint, a more flexible fibrous mat is cut to approximate the entire joint surface, then fitted to the surgically prepared recipient joint as necessary during implantation. In the preferred embodiment, the joint is cleaned of existing cartilage, mesh seeded with chondrocytes is used to line the joint, then mesh not seeded with chondrocytes is sutured over the seeded mesh, to secure and protect the chondrocytes until the cells proliferate, remodel and the resulting cartilage structure is integrated with the surrounding host tissue and bone. An apparent advantage of using the fibrous matrices is the ease in reshaping and rearranging the structures at the time of implantation.

A sponge-like structure can also be used. The structure should be an open cell sponge, one containing voids interconnected with the surface of the structure, to allow adequate surfaces of attachment for sufficient cells to form a viable, functional implant.

An advantage of the present invention is that, using similar technology, other components of the nose, ear and joints can be constructed using bone and nerve precursor cells. For example, matrices in the shape of the bones of the inner ear can be formed by casting the polymer to form hollow shapes of the appropriate size and configuration, then seeding with bone precursor cells, culturing in vitro as required, then implanting into an ear canal. The major portion of the eustachian tube and inner ear is made of cartilage. The technology is equally applicable to manufacture of an ear drum or skin for covering the implanted cartilage. Nerve cells can also be implanted within or in juxtaposition with the reconstructed ear.

The matrix is sterilized prior to mixing with the cells using methods known to those skilled in the art for the matrix material. Materials such as the biodegrables polymers are sterilized with ethylene oxide, carefully removed by degassing prior to mixing the matrix with the cells. Materials such as teflon or nylon can be autoclaved.

Cells may be derived from the host, a related donor or from established cell lines. In one variation of the method using a single matrix for attachment of one or more cell lines, the scaffolding is constructed such that initial cell attachment and growth occur separately within the matrix for each population, for example, bone precurser and chondrocyte cell populations. Alternatively, a unitary scaffolding may be formed of different materials to optimize attachment of various types of cells at specific locations. Attachment is a function of both the type of cell and matrix composition. Chondrocytes obtained from biopsy may be either elastic cartilage or hyaline cartilage.

These cell-matrix structures are useful not only for in vivo implantation, but also for the production of bioactive molecules in vitro, such as the proteinase inhibitors reported by Bunning, et al., *Wur. J. Biochem.* 139, 75–80 (1984) and Roughley, et al., *Biochem. J.* 169, 721–724 (1978), and collagenase inhibitor reported by Langer, et al., *Science* 191, 70–72 (1976).

The following non-limiting examples demonstrate actual attachment of cell preparations to bioerodible artificial polymers in cell culture and implantation and engraftment of this polymer-cell scaffold into animals. The examples further demonstrate that the cells attached to the matrix function normally and secrete bioactive molecules, such as angiogenesis inhibiting factor, and can therefore be used for the in vitro production of such molecules.

EXAMPLE 1

Demonstration of the Method for Production of Cartilage Structures in vivo from Polymeric Matrices Prepared in vitro FIGS. 1a and 1b demonstrate the method of the present invention for production in vivo of facial contour plates. Chondrocytes were isolated from cartilage and and a dispersion prepared using standard techniques similar to those discussed below. Surgical mesh (Dexon™, a fibrous polyglycolic acid mesh) was seeded with the chondrocytes and the cells allowed to incubate until the chondrocytes attached. The matrix was then implanted on the head of a nude mouse, as shown in FIG. 1a. Five to six weeks later, cartilage plates had formed, as shown in FIG. 1b.

EXAMPLE 2

Isolation of Chondrocytes from Cartilage and Analysis of Cartilage Formation on a Seeded Matrix in vitro and in vivo Over Time, and Lack of Formation of Cartilage in the Absence of a Matrix Articulating cartilage was obtained from the shoulders of calves under two weeks of age slaughtered earlier in the day. The shoulders were washed in Povidone-Iodine 10% solution (Betadine, Purdue Frederick Co., Norwalk, Conn.), then, under sterile conditions, the muscle attachments were sharply dissected from the underlying bone to expose the joint surfaces. The cartilage from the articulating surfaces of the joint were then sharply dissected from the underlying bone using a #10 scalpel (Bard-Parker, Rutherford, N.J.). The cartilage was cut into pieces with dimensions of less than 5 mm per side and washed twice in Phosphate Buffered Saline (PBS) with electrolytes and adjusted to neutral pH. The cartilage was then incubated at 37° C. in a solution of 0.2% clostridial collagenase (Worthington CLS II, 140 U/mg) and agitated overnight as described by Klagsbrun, (*Methods in Enzymology*, Vol. VIII). This suspension was then filtered using a 153 µg nylon sieve (Tetko, Elmford, N.Y. 10523). The cells were then removed from the suspension using centrifugation, washed twice with PBS solution and counted with a hemocytometer. The solution was centrifuged at 1800 rpm and the supernatant above the cell suspension was removed via suction using a micropipette until the volume of the solution yielded a chondrocyte concentration of $5 \times 10^7$ cells/cc.

Braided threads of polyglactin 910, a 90-10 copolymer of glycolide and lactide, coated with polyglactin 370 and calcium stearate ("0" Vicryl™ suture material, Ethicon, Inc., Somerville, N.J.) were then cut into pieces of approximately 17 mm in length. One end was unbraided to expose multiple fibers, 14 microns in diameter. A knot was placed at the other end to aid in locating the polymer during subsequent biopsy. Two polymer fibers were placed into each of 26 Falcon tissue culture dishes, 35 mm in size. Two hundred μL of the above solution was placed on the two fibers in each of 15 wells, thus exposing 30 fibers to the solution containing chondrocytes (the experimentals) and keeping 22 polymers free from exposure to chondrocytes (the controls). Next, 2 cc of a solution containing Hamm's F-12 culture media and 10% fetal calf serum with L-glutamine (292 μg/cc), penicillin (100 U/cc), streptomycin (100 μg/cc) and ascorbic acid (5 μg/cc) was added to each well. After being incubated at 37° C. for 3, 6, 11, 18, 21 and 28 days, six fibers from each group were examined for the presence and morphologic appearance of chondrocytes using phase contrast microscopy and then evaluated histologically using Hematoxylin and Eosin staining and Aldehyde-Alcian Fuschin stain for chondroitin sulfate, the strongly acidic sulfate of mucopolysaccharides of the cartilage.

Figure 2:
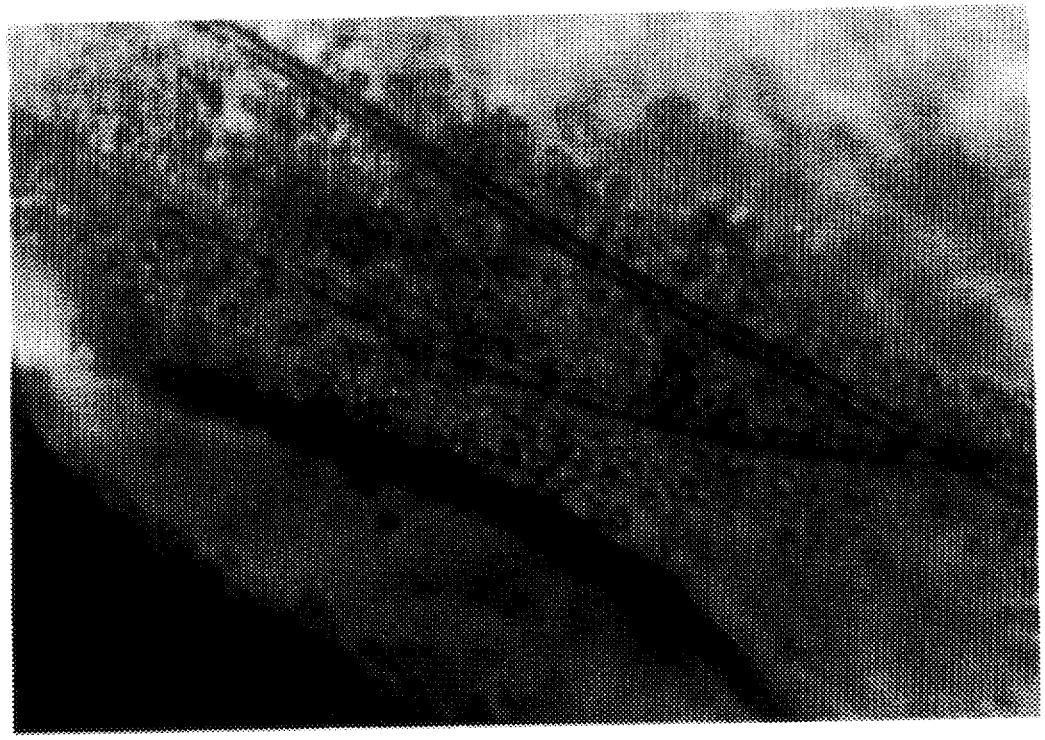
FIG. 2 is a phase contrast photomicrograph of bovine chondrocytes attached to two polymer fibers three hours after seeding the fibers.
Figure 3:
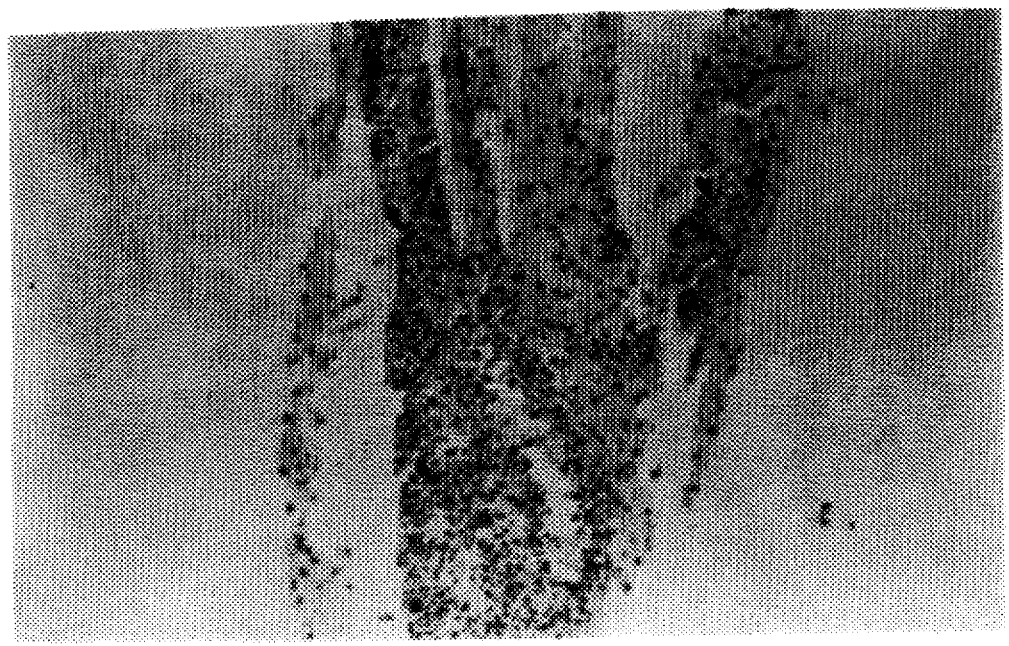
FIG. 3 is a photograph of Hematoxylin and Eosin stained chondrocytes after 10 days in culture.
Figure 4A:
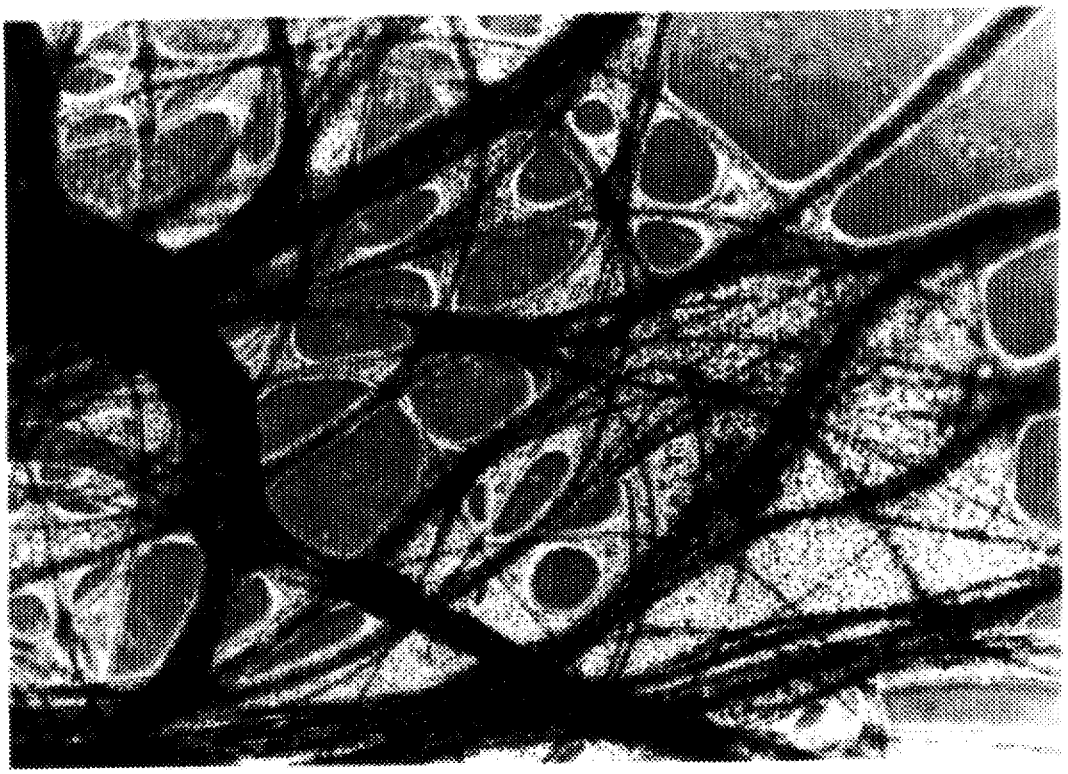
FIG. 4a and 4b are phase micrographs of chondroxytes attached to the polymer fibers after 21 days in culture.
Figure 4B:
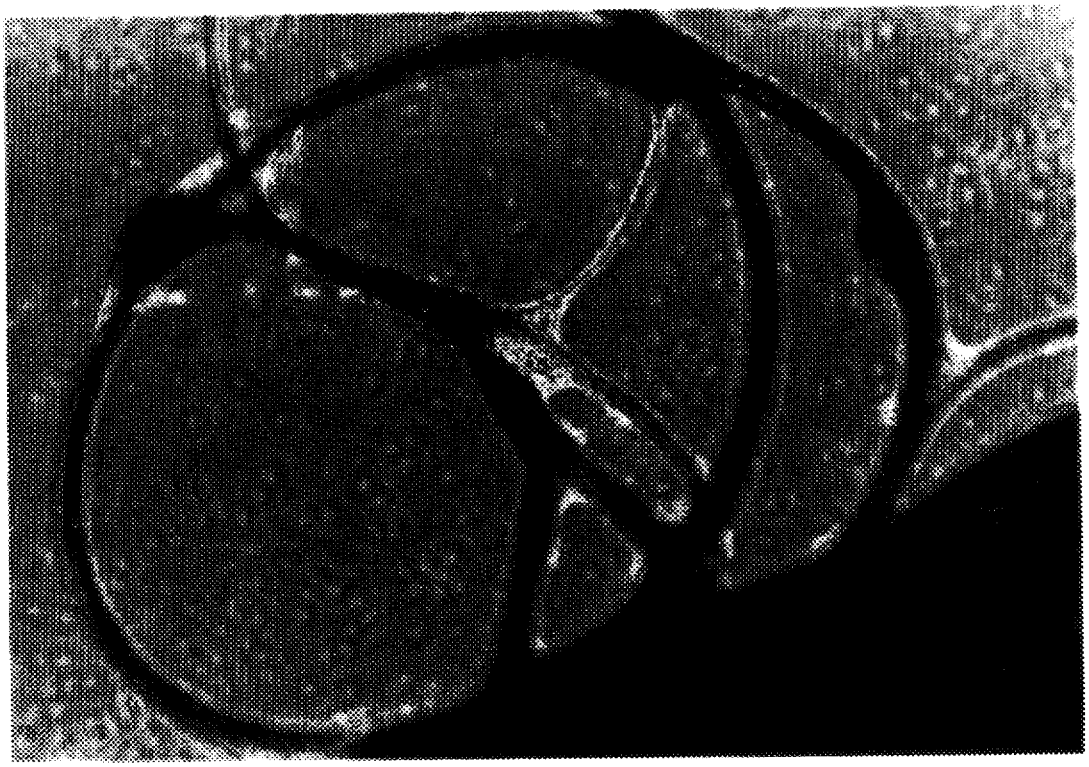

FIG. 2 is a phase contrast photomicrograph of bovine chondrocytes attached to two polymer fibers three hours after seeding the fibers. It is important to note that the chondrocytes appear round, their normal configuration. This configuration is necessary for secretion of the components of cartilage. FIG. 3 is a photograph of the cells stained with Hematoxylin and Eosin after 10 days in culture. FIG. 4a and 4b are phase micrographs of the cells attached to the polymer fibers after 21 days in culture. It appears that the chondrocytes cause the fibers to bend on themselves and come into contact with other chondrocytes. FIG. 4a is a 4× magnification showing the very high density of chondrocytes filling in the spaces between the polymer fibers. FIG. 4b is a 20× magnification showing that when the chondrocytes come to the end of a polymer fiber they seem to multiply to a certain density and form what looks like a node. After 24 days in culture, the matrix between these cells stained basophilic by hematoxylin Eosin staining, demonstrating the presence of cartilage. The cells are further spaced apart after 24 days in culture than after 10 days. Phase microscopy of cells after four weeks in culture shows the chondrocytes bridging the distances between the polymer fibers.

The remaining forty fibers (24 experimental and 16 control) were surgically implanted subcutaneously on the dorsum of 40 male nude mice (Athymic NCr/nude/Sde, Dept. of Radiation Medicine Massachusetts General Hospital, Boston, Mass.), four to five weeks of age, in the midline at the base of the neck. Thirty-five of these implants (19 experimentals and 16 controls) were done after the fibers had been incubated for three days in vitro, while the remaining five implants, all experimentals, were done after incubating the fibers for 10 days in vitro. Five mice with implants (one control, one with chondrocytes incubated for 10 days and three with chondrocytes incubated for three days) were sacrificed at each of the following intervals: 8, 18, 28, 49 and 81 days. The implants were then excised from the surrounding tissue with sharp dissection utilizing a tissue plane which easily separated the implant from the surrounding tissue. The specimens thus included primarily implanted tissue and minimal endogenous tissue from the animal.

Each specimen was fixed in formalin, weighed, and its volume calculated by measuring the volume of a liquid which it displaced. Their weights and volumes were correlated and plotted against time. All specimens were evaluated grossly and histologically, using Hematoxylin and Eosin stains as well as an Aldehyde-Alcian Fuschin stain for the presence of chondroitin sulfate, a major component of cartilage.

Figure 5:
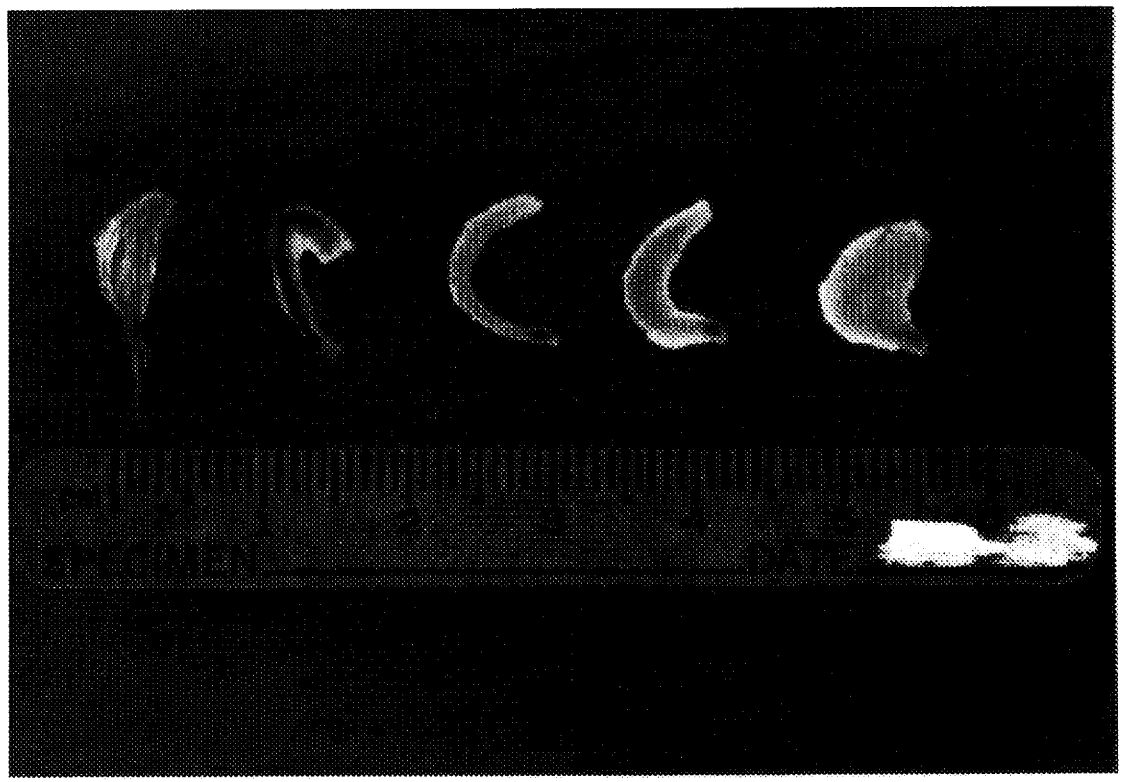
FIG. 5 is a photomicrograph of polyglactin 910 fibers shaped and seeded with bovine chondrocytes and cultured in nude mice, after 8, 18, 28, 49 and 81 days.
Figure 6:
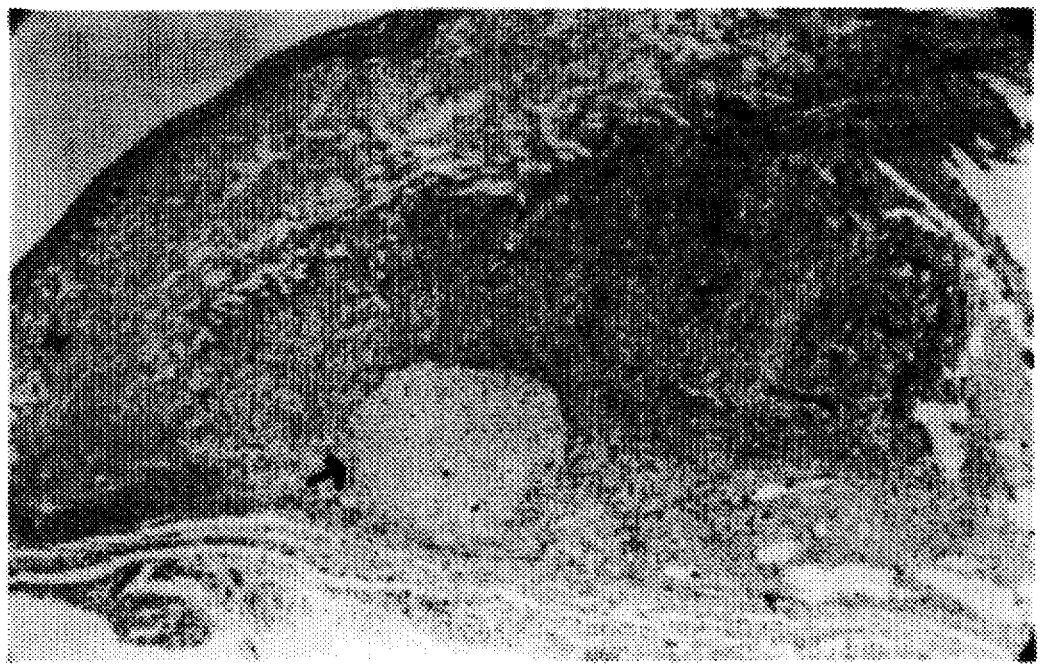
FIG. 6 is a photograph at 4× of Hematoxylin and Eosin stained chondrocytes showing a small island of cartilage at the arrow eight days after implantation.
Figure 7:
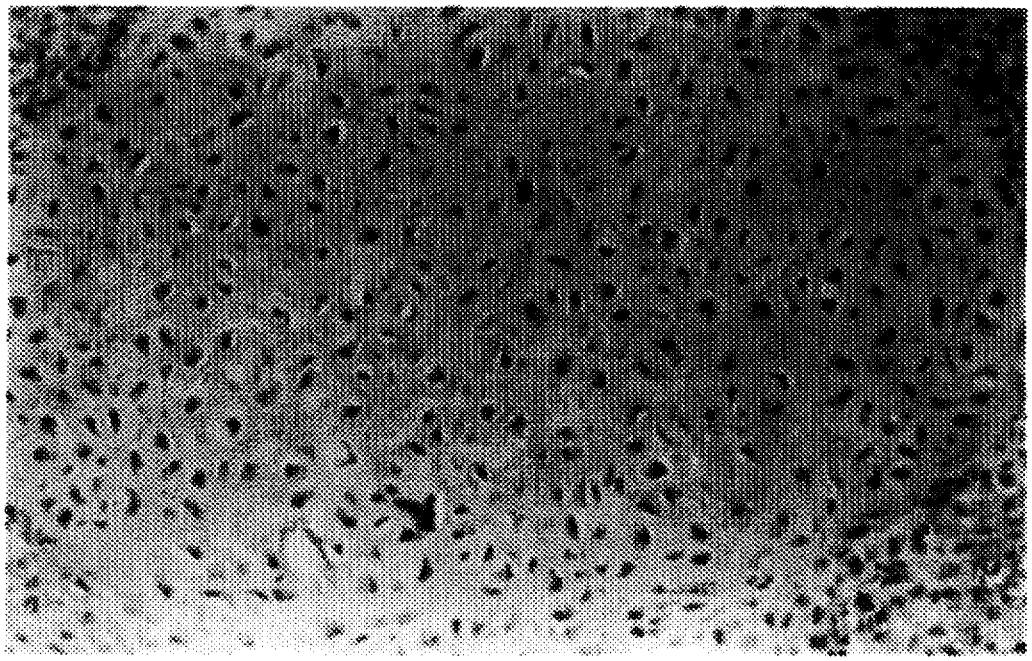
FIG. 7 is a photograph at 20× of the cartilage island of FIG. 6.
Figure 8:
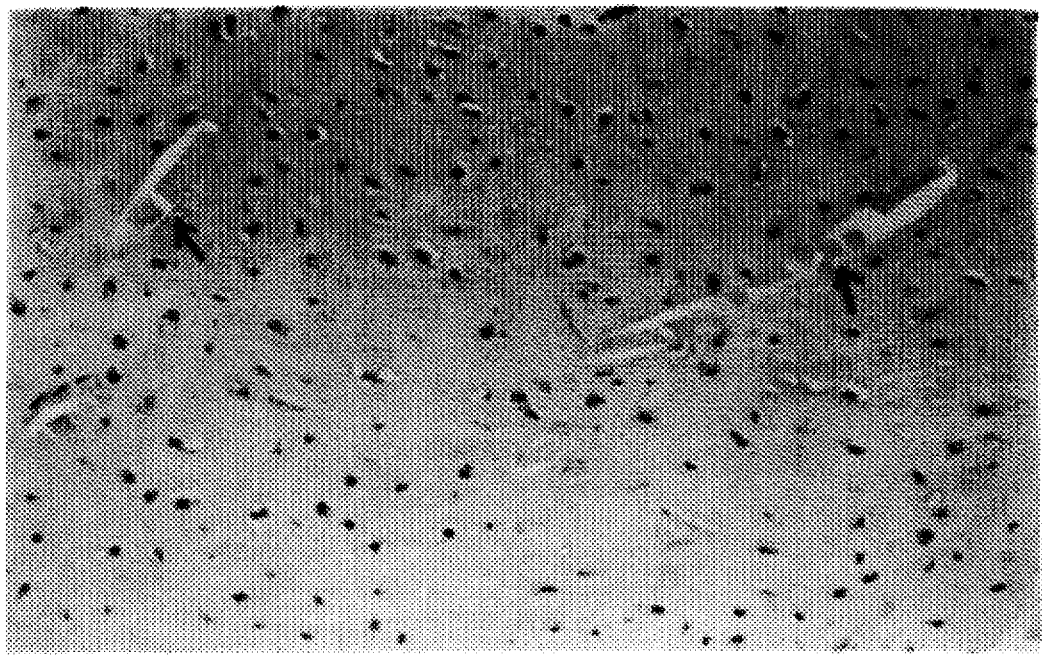
FIG. 8 is a photograph at 20× of Hematoxylin and Eosin stained chondrocytes on a polymeric matrix 28 days after implantation, showing the polymers being absorbed by the surrounding tissue.
Figure 9A:
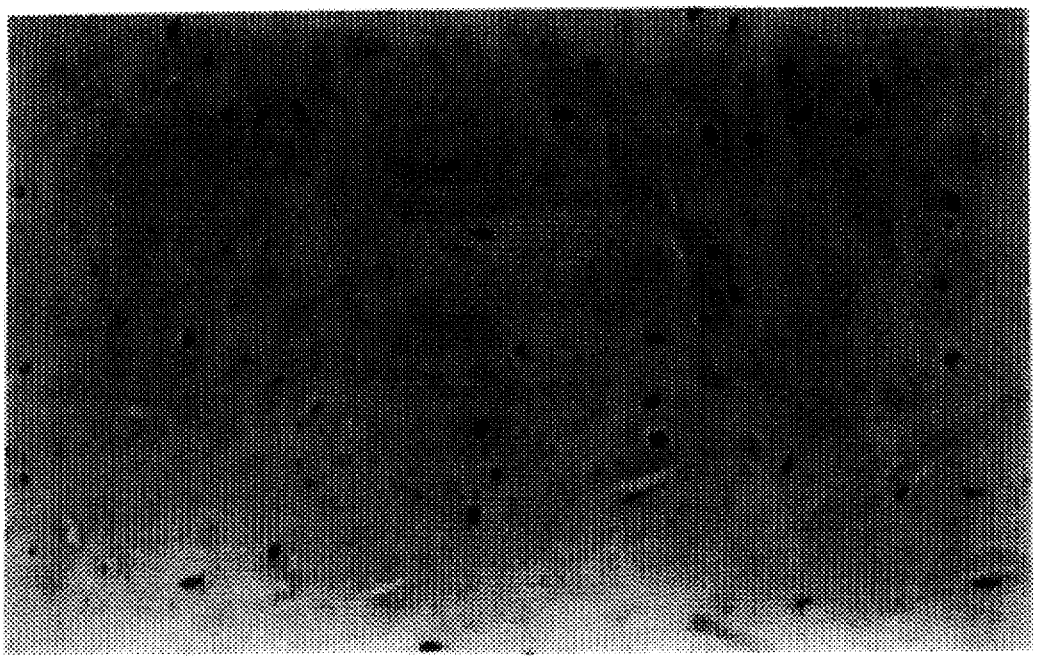
FIGS. 9a and 9b are photographs of Hematoxylin and Eosin stained chondrocytes 81 days after implantation in an animal.
Figure 9B:
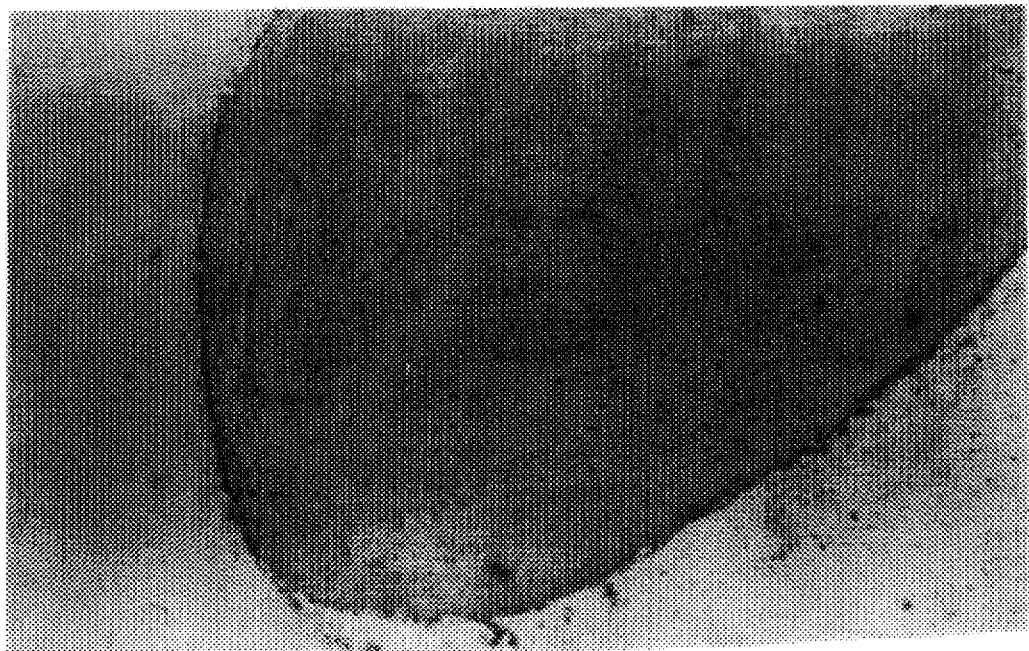

FIG. 5 is a photomicrograph of polyglactin 910 fibers seeded with bovine chondrocytes and cultured in nude mice, after 8, 18, 28, 49 and 81 days. FIG. 6 is a 4× photograph of Hematoxylin and Eosin stained cells after 8 days implantation showing a small island of cartilage at the arrow. FIG. 7 is a photograph at 20× of the cartilage island of FIG. 6. FIG. 8 is a photograph at 20× of an implant after 28 days, showing the polymers being absorbed by the surrounding tissue. FIG. 9a is a photograph at 20× after implantation in an animal for 81 days. FIG. 9b is the same implant at 4×, looking very similar to normal human fetal cartilage at 10 weeks.

In a control study, ten mice were injected subcutaneously in the same region with a 200 μL suspension containing $5 \times 10^5$ chondrocytes, without attachment to polymers. Five of these suspensions contained chondrocytes isolated primarily from the calf shoulder and then injected into the mice. The other five suspensions contained chondrocytes obtained at the same isolation and then incubated in vitro for three days prior to injection. These mice were sacrificed at similar time intervals, and the areas injected were evaluated histologically in the same manner for evidence of chondrocytes or cartilage.

The results demonstrate that chondrocytes attach to synthetic biodegradable polymer fibers in cell culture and proliferate to a cell density sufficient to allow implantation of the cell polymer scaffold in animals with successful engraftment and cartilage formation. Fibers of polyglactin 910 incubated in culture media in the presence of bovine chondrocytes had chondrocytes adhering to them and were surgically implanted subcutaneously on the dorsum of twenty nude mice. As controls, sixteen sets of fibers, incubated in media not containing chondrocytes, were implanted in the same manner into sixteen nude mice and ten mice were injected with 0.2 cc of culture media containing $5 \times 10^5$ chondrocytes in the same area.

The three groups of mice were sacrificed at 8, 18, 28, 49 and 81 days and the implants were evaluated grossly and histologically. In eighteen of the twenty implants with chondrocytes adhering in vitro, there was histologic evidence of cartilage which progressed over the time course of this study and was indistinguishable in appearance to normal human fetal cartilage. Furthermore, over the time course of this study, the polymer fibers dissolved, beginning by day 27, and, utilizing Hematoxylin and Eosin staining, as well as Aldehyde-Alcian Fuschin stains, the cartilage progressed histologically from being isolated islands of cartilage in the presence of fibrous tissue and neovascularization at day 8, to becoming a homogenous mass of cartilage. Neovascularization of the implant with mild inflammation was seen initially, but over time, the new blood vessels regressed as cartilage matrix was laid down and intercellular chondrocyte distances increased as they do with normal cartilage maturation. The decrease in inflammatory response, as evidenced by decreases in the number of polymorphonuclear leukocytes and giant cells, correlated with the disappearance of the polymers. There was very little evidence of either inflammatory response or polymer remnants by day 81.

There was no evidence of cartilage present in any of the control polymeric implants, as determined histologically using Hematoxylin and Eosin stain. A mild inflammatory response with polymorphonuclear leukocytes, giant cells, and fibroblasts was noted until day 28, after which there was no evidence of the implant. Cartilage formation was also not evident in any area injected with chondrocytes in suspension.

In conclusion, the chondrocytes readily adhere to the polymer fibers. The six experimental fibers incubated in vitro with chondrocytes were seen microscopically to have multiple layers of chondrocytes adhering to them sufficiently well that gentle agitation of the complex did not lead to dissociation of the cells from the fibers. The cells appeared to remain in their normal rounded configuration and analysis of the media in which they were grown demonstrated that angiogenesis inhibiting factor was produced by these cells. The number of chondrocytes as well as the number of layers of chondrocytes adhering to the polymer fibers appeared to increase progressively with time and appeared to actively remodel the fiber configuration and bridge small distances between the fibers. The six control fibers incubated in vitro without chondrocytes showed no evidence of chondrocytes on histologic evaluation. In vitro, all polymer fibers (controls and experimentals) began to dissolve by day 27. On gross and histologic examination using Hematoxylin and Eosin stain, none of the 16 specimens designated as controls displayed any evidence of cartilage. In contrast, 18 of 20 specimens in the experimental group showed evidence of cartilage formation grossly, as well as histologically using Hematoxylin and Eosin stain. Histologic examination of the implants removed at day 8 showed the fibers were imbedded in fibrous tissue with evidence of a mild inflammatory response consisting of infiltrates of polymorphonuclear leukocytes and giant cells, and isolated "nests" of cartilage. During the time intervals to day 18 and day 28, these islands of cartilage grew and coalesced into a large homogenous mass of cartilage. There was no evidence of neovascularization in the 49- and 81-day implants, and there was decreasing evidence of an inflammatory response with time as characterized by a decrease in the number of polymorphonuclear leukocytes and giant cells. Very little evidence of the polymer fibers was seen after 28 days. This increase in the size of the cartilage appeared to be at the expense of the fibrous tissue previously seen and associated at least temporarily with a decrease in neovascularization and resolution of the mild inflammatory response originally noted. Also associated with this was the absorption of the biodegradable polymer fibers. In time, the polymer fibers were progressively replaced by cartilage, until only cartilage with very little evidence of polymer remained and the specimens became a homogeneous mass of cartilage histologically very similar to normal human fetal cartilage. There was a very positive correlation between the weights and volumes in both groups, with a rapid decline in the weights and volumes of the control implants with time after an initial increase in size. The weights and volumes of the experimentals (those polymers with attached chondrocytes) initially paralleled the increase seen in the controls, but then seemed to level off at a stable size by day 49. In the second group of controls, the injections of free chondrocytes in suspension, there was no evidence of cartilage formation in any of the areas injected.

EXAMPLE 3

Figure 10B:

Method of Implantation of Matrices Seeded with Chondrocytes and Growth of Hyaline Cartilage for Joint Relinings The distal femur of a New Zealand white rabbit was relined with new hyaline cartilage. As shown in FIG. 10a, a surgical Dexon™ mesh seeded with chondrocytes attached in culture was implanted into the surgically prepared knee joint of the rabbit, then overlaid with mesh not seeded with chondrocytes. The knee was prepared by grinding or slicing off all of the existing cartilage. The overlaying mesh is sutured over the seeded mesh to secure and protect the chondrocytes until they proliferate and form a new lining, as shown five weeks after implantation, in FIG. 10b.

The cartilage appears, both grossly and histologically, to adhere to the underlying bone in a manner consistant with a normal cartilage-bone interface. Analysis of the newly grown cartilage via immunochemistry using the avid-biotin-peroxidase complex technique has demonstrated the presence of type II collagen, and the absence of type I collagen. This is significant in that type II collagen is found almost exclusively in hyaline cartilage, while type I is absent in normal hyaline cartilage.

The number of cells needed for implantation to optimally repair a defect in hyaline articular cartilage. The calculations are based on known concentrations of chondrocytes per unit mass of hyaline articular cartilage and the actual counts of the number of chondrocytes present in the cartilage removed when creating a defect of known size. If necessary, the chondrocytes obtained from biopsy can be multiplied in vitro prior to attaching the optimal number of cells to the polymers after implantation.

EXAMPLE 4

Growth of Normal Elastic Cartilage in vivo from Matrices Seeded with Chondrocytes Chondrocytes obtained from biopsy of human elastic cartilage was attached to polymer fibers in vitro and implanted. Histologically normal elastic cartilge grew in the approximate dimensions of the implanted complex.

EXAMPLE 5

Implantation of Chondrocytes on a Matrix for Repair of a Bone Defect and Subsequent Formation of "Bone"

A defect in the tibia of a New Zealand white rabbit of approximately twice the radius of the bone was created. The periosteum was removed at the site of the defect. Polymer mesh was seeded with chondrocytes as described above, and implanted into the defect. Histology and chemical analysis can be used to confirm that the implant formed bone. In controls using the same model without the seeded implant, the defect fills with fibrous tissue rather than bone.

Although this invention has been described with reference to specific embodiments, variations and modifications of the method and means for constructing cartilage implants by culturing chondrocytes on matrices having maximized surface area and exposure to the surrounding nutrient-containing environment will be apparent to those skilled in the art. Such modifications and variations are intended to come within the scope of the appended claims.

We claim:

1. A cell-scaffold composition for growing cells to produce a functional cartilaginous structure in vivo, comprising:

a fibrous three-dimensional scaffold composed of fibers of a biocompatible, biodegradable, synthetic polymer; and cartilage-producing cells attached to the surface of the fibers of the scaffold uniformly throughout the scaffold;

wherein the fibers of the scaffold are spaced apart such that the average interfiber distance is between approximately 100 and 300 microns;

wherein the fibers of the scaffold provide sufficient surface area to permit attachment of a density of cells effective to produce the functional cartilaginous structure in vivo; and wherein the diffusion in the scaffold provides free exchange of nutrients, gases and waste to and from the cells uniformly attached to the fibers and proliferating throughout the scaffold in an amount effective to maintain cell viability throughout the scaffold prior to the formation of the functional cartilage in vivo.

2. The cell-scaffold composition of claim 1 wherein the polymer is selected from the group consisting of polyanhydrides, polyorthoesters, polyglycolic acids, polylactic acids, copolymers, and blends thereof.

3. The cell-scaffold composition of claim 1 wherein the scaffold is formed of a combination of biodegradable and non-biodegradable materials.

4. The cell-scaffold composition of claim 3 wherein the non-degradable material is selected from the group consisting of polytetrafluoroethylene, nylon, ethylene vinyl acetate, polyesters and combinations thereof.

5. The cell-scaffold composition of claim 1 further comprising a coating(s) on the fibers selected from the group consisting of basement membrane components, agar, agarose, gelating, gum arabic, collagens, fibronectin, laminin, hyaluronic acid, glycosaminoglycans, attachment peptides and mixtures thereof.

6. The cell-scaffold composition of claim 1 wherein the scaffold forms a rigid structure.

7. The cell-scaffold composition of claim 1 wherein the scaffold forms a flexible structure conformable to a joint surface.

8. The cell-scaffold composition of claim 1 wherein the cells are chondrocyte cells.

9. The cell-scaffold composition of claim 1 wherein the structure is a joint lining.

10. The cell-scaffold composition of claim 1 wherein the cartilage-producing cells are fibroblasts capable of differentiation into chondrocytes.

11. The cell-scaffold composition of claim 1 wherein the cartilage precursor cells are bone precursor cells capable of differentiation into chondrocytes.

12. The cell-scaffold composition of claim 1 wherein the fibers form an open-cell sponge containing voids interconnected with the surface of the scaffold.

13. The cell-scaffold composition of claim 1 wherein the polymer is selected from the group consisting of polymers degrading by hydrolysis and polymers degrading enzymatically, and the scaffold fibers are separated by a distance sufficient to allow multiple layers of cells to adhere to the surface of the fibers and to provide free exchange by diffusion of nutrients and waste to the attached cells throughout the scaffold when the cells on the scaffold are cultured in a nutrient media.

14. A cell-scaffold composition comprising a fibrous three-dimensional scaffold composed of fibers of a biocompatible, synthetic polymer and cartilage-producing cells uniformly attached to the surface of the fibers throughout the scaffold, wherein the scaffold fibers are separated by a distance sufficient to allow multiple layers of cells to adhere to the surface of the fibers and to provide free exchange by diffusion of nutrients and waste to the attached cells throughout the scaffold when the cells on the scaffold are cultured in a nutrient media, and wherein the scaffold is in the form of an ear or a component thereof.

15. A cell-scaffold composition comprising a fibrous three-dimensional scaffold composed of fibers of a biocompatible, synthetic polymer and cartilage-producing cells uniformly attached to the surface of the fibers throughout the scaffold, wherein the scaffold fibers are separated by a distance sufficient to allow multiple layers of cells to adhere to the surface of the fibers and to provide free exchange by diffusion of nutrients and waste to the attached cells throughout the scaffold when the cells on the scaffold are cultured in a nutrient media, and wherein the scaffold is in the form of a nose or a component thereof.

* * * * *